United States Patent

Campagnolo et al.

[11] Patent Number: 6,035,706
[45] Date of Patent: Mar. 14, 2000

[54] METHOD AND APPARATUS FOR DETERMINING THE WAX APPEARANCE TEMPERATURE OF PARAFFINIC PETROLEUM OILS

[75] Inventors: Eugenio André Campagnolo; Reinaldo Washington Ferreira Santos; Valter Antonio Monteiro Branco, all of Rio de Janeiro, Brazil

[73] Assignee: Petroleo Brasileiro S.A. - Petrobras, Rio de Janeiro, Brazil

[21] Appl. No.: 08/864,065

[22] Filed: May 28, 1997

Related U.S. Application Data

[63] Continuation of application No. 08/626,005, Apr. 1, 1996, abandoned.

[30] Foreign Application Priority Data

Apr. 28, 1995 [BR] Brazil ..................................... 9501855

[51] Int. Cl.[7] .......................... G01N 33/28; G01N 25/02
[52] U.S. Cl. ............................................. 73/64.42; 374/23
[58] Field of Search ............................. 73/61.43, 61.41, 73/61.49, 64.41, 64.42; 374/16, 22, 23, 55, 56

[56] References Cited

U.S. PATENT DOCUMENTS

5,247,828   9/1993   Candau et al. .......................... 73/64.42

FOREIGN PATENT DOCUMENTS

2268276   1/1994   United Kingdom .
WO9520153  7/1995   WIPO .

OTHER PUBLICATIONS

Jacoby et al. "PVT Measurements on Petroleum Reservoir Fluids and Their Uses", Industrial and Engineering Chemistry, vol. 59, No. 10, Oct. 1967.

*Primary Examiner*—Michael Brock
*Attorney, Agent, or Firm*—Sughrue, Mion, Zinn, Macpeak & Seas, PLLC

[57] ABSTRACT

A method and apparatus for determining the wax appearance temperature of paraffinic petroleum oils which comprises measuring and plotting the density of the paraffinic oil as a function of temperature at constant pressure, with the wax appearance temperature being indicated by the inflection point of the graph.

7 Claims, 6 Drawing Sheets

METHOD AND APPARATUS FOR DETERMINING THE WAX APPEARANCE TEMPERATURE OF PARAFFINIC PETROLEUM OILS

CROSS REFERENCE TO RELATED APPLICATION

This application is a continuation of U.S. application Ser. No. 08/626,005, filed Apr. 1, 1996 now abandoned.

BACKGROUND OF THE INVENTION

1. Field of the Invention

The present invention relates to a method and the corresponding apparatus used to determine the wax appearance temperature or cloud point of waxy or paraffinic petroleum oils. More specifically, the present invention relates to a method to determine the wax appearance temperature of paraffinic petroleum oils by measuring the change in density of the petroleum oil at the wax appearance temperature by means of a Pressure-Volume-Temperature (PVT) cell coupled to a high pressure and temperature densimeter.

Throughout the present specification, the terms "petroleum oils" and "fluid" represent hydrocarbon fluids as present in the reservoir, with or without gas dissolved therein.

Generally, the composition of oils and hydrocarbon fluids is of such complexity that it is difficult to estimate the number of components of such fluids. However, it is usual to consider the presence of straight-chained (n-paraffins) and branched paraffins (iso-paraffins), naphthenes (cycloparaffins) and aromatic compounds. Besides, there are further small amounts of compounds such as asphaltenes and resins which include heteroatoms and heavy metals.

It is also important to distinguish between dead oil (without gas) and live fluid (with gas, such as occurs in a reservoir). The content of light hydrocarbons ($C_1$ to $C_6$) in live fluid is in the order of 20 mol % higher than for dead oil.

For the straight-chained paraffins, the change in physical properties is proportional to the increase in chain length. The branched paraffins have less predictable properties. An increasing level of branching will, in most cases, lead to a reduction in the boiling point and melting point. The composition of paraffins in each oil is a function of factors such as the geological origin of the oil. For wax appearance this means that it is very difficult to characterize the material appearing. The wax which appears will mainly be normal paraffins on account of the higher content of these components and because the melting points for n-paraffins are considerably higher than for most other components in the oil. Models which are based on a wax fraction which is dissolved in the rest of the oil must therefore have a good analytical description of the composition of the complete fluid, in both its solid and liquid phases.

It is common knowledge that the content of light components in the fluid exerts an influence on the solubility of the longer chain components at a given temperature. Besides, the increase in pressure, as a function of a higher content in light components, will affect the properties of the components in the oil and thus also the solubility. Thus the overall effect of higher pressure and higher content in light components will depend on the total composition of the fluid.

On the other hand, the improvement in the exploration of paraffinic oil reservoirs necessarily involves a mathematical model which would represent the behavior of such oils as concerns their flow in porous media and pipelines as well as the thermodynamic balance of the gas, liquid and solid phases, the latter phase having origin in the paraffins which crystallize out from solution.

The development of the model requires that the behavior of the fluid in some of the conditions where the real phenomenon occurs in the reservoir or in the pipelines, be known. Once this behavior is adjusted, the model can be applied to effect simulations and determine the fluid behavior in any condition.

To determine the wax appearance point or cloud point of an oil at different compositions, the influence of pressure on the wax appearance point and a study on the reversibility of the process are of paramount importance for the modelling of a paraffinic oil or a hydrocarbon fluid.

2. Description of the Related Art

According to the ASTM Standard Test No. D2500-91 the wax appearance point is determined by the direct visualization of the formation of waxy or paraffinic crystals in the fluid within a transparent vessel kept in a controlled temperature bath. Because a mist or cloud is developed in the fluid, the wax appearance point is also known as its cloud point. The above mentioned ASTM Standard is limited to clear fluids.

In the technique known as Differential Scanning Calorimetry, or DSC, the measurement of the heat released during the solidification of the paraffin crystals is the basis for determining the cloud point. However, this technique can yield lower than real figures for wax appearance point, mainly in the case of petroleum oils of low paraffin content.

In the optical microscopy process, the measurement of the wax appearance point is obtained by detecting the appearance of the paraffin crystals on the thin layer of an optical microscope. This thin layer is coupled to a system of controlled cooling. The polarized light reaching the thin layer renders easier to detect the onset of wax appearance. The preparation of a thin layer (50 micrometers) and the incidence of light render it possible to use opaque fluids such as petroleum oils. While the optical microscopy method provides wax appearance points with reasonable accuracy, it is not a very practical method as an everyday, routine analytical tool.

In another approach, the viscosity is determined at several temperatures. The cloud point is identified by an inflection on the viscosity vs. temperature curve. As in the DSC technique, this technique can equally yield figures for wax appearance point which are inferior to the real ones.

GB-A-2268276 describes a method of determining the wax appearance point in a petroleum product wherein the petroleum volume is measured and plotted as a function of temperature at constant pressure, wherein the wax appearance point of the waxy or paraffinic phase occurs at the temperature at which there is a deviation in the graph. The method described in GB-A-2268276 comprises further determining the quantity of wax in a petroleum product at a particular temperature below the wax appearance point by (i) estimating the density of the solid and liquid wax, (ii) measuring the change in volume of the petroleum product due to the formation of solid wax phase, and (iii) multiplying the difference of the density of the wax in the two phases as determined by the measured volume change.

According to British GB-A-2268276 phase changes in the fluid derive from a temperature variation. The alleged advantage lies in the fact that the measurement of certain fluid properties can be directly explained by the transition from liquid phase to solid phase. The apparatus used in the method of the British publication comprises a pressure cell placed in a thermostatic bath, a pump connected to the pressure cell to produce pressure, sensors to determine pressure, temperature and volume in the cell and a control unit to read and set the cell pressure, temperature and volume.

However, it has been found that, since the accuracy of volumetric measurements by pumps such as the ones described in GB-A-2268276 is of 0.01 cm$^3$, then for a 60 cm$^3$ sample described in FIG. 2 of the publication, the lowest detectable volume contraction is (0.01 cm$^3$ in 60 cm$^3$)=0.017%, this order of magnitude being present only for the wax appearance point of highly paraffinic oils. Thus, the method described in GB-A-2268276 is in practice limited to highly paraffinic oils. Besides, there are drawbacks involved in preparing several samples of 60 cm$^3$ each, having varying amounts of gas, in order to vary the oil composition and thus determine the influence of the composition on the wax appearance point. In order to determine the influence of the composition on the wax appearance point it is necessary to have at least 1000 cm$^3$ of oil which must be solubilized with varying amounts of gas.

Therefore, there is the need for a method and high-precision apparatus to determine the wax appearance point of oils with a wide range of paraffinic contents, including contents as low as 0.5 wt %, using small volume samples, the measurements being effected in short periods of time, these advantages being presented by the present application.

SUMMARY OF THE INVENTION

Accordingly, one aspect of the present invention provides a method for determining the wax appearance temperature of paraffinic petroleum oils, comprising measuring and plotting the density of the petroleum oil as a function of the temperature at constant pressure, and determining the wax appearance point as the temperature at which there is an inflection in the graph.

Thus, the method of the present invention comprises determining the temperature of wax appearance point of paraffin crystals of petroleum oils and related products, the oil being stabilized under atmospheric conditions (dead oil) or containing solubilized gas (live fluid).

Basically, the method of the present invention comprises measuring the density of the petroleum oil at various temperatures and plotting the figures on a graph. Contrary to non-paraffinic oils where the behavior of the density is practically linear at all temperatures, for oils showing some paraffinic content there is a portion of linear behavior at higher temperatures and a portion, at lower temperatures, where the behavior is no longer linear and an increase in density occurs as compared with the prolonging of the linear behavior. The temperature where the linear behavior ceases is considered as the temperature of the wax appearance point. The increase in density is associated with the shrinking of the fluid, which is caused by the fact that paraffin molecules get nearer to each other during the wax appearance. The density of the fluid is measured using a high pressure and temperature densimeter.

The present invention comprises further determining the influence of the dissolved gas on the wax appearance point of pressurized fluids.

Thus, one objective of the present invention is a high precision method for determining the temperature of wax appearance point of oils with or without gas in solution (live fluid or dead oil respectively), the oils containing from 0.5 wt % of waxes or paraffins, by measuring the change in density of the fluid as a function of temperature by means of a high temperature and pressure densimeter.

Another objective is to determine the influence of the dissolved gas as quantified by the solubility ratio Sr, on the wax appearance point of pressurized fluids. For such purpose, the densimeter is coupled to a Pressure-Volume-Temperature cell which is an apparatus in which a mercury piston permits the pressure and the volume of the fluid within the cell to be varied.

Still another objective is a high-precision apparatus for determining the wax appearance point of oils showing wax or paraffin content of from 0.5 wt % upwards, the oil having or not having gas dissolved therein (live fluid or dead oil respectively), the apparatus consisting basically of a vessel or bottle capable of withstanding pressure and temperature and which is coupled to a high-precision densimeter.

A second aspect of the invention provides an apparatus for use in the method of the first aspect, which comprises a bottle to contain the sample of paraffinic oil, a mercury pump for evacuating the bottle and a high pressure and temperature densimeter connected to the bottle for determining the variation in density of the sample with the temperature reduction, wherein the densimeter has its temperature regulated by an ultrathermostatic bath, and wherein the bottle, the mercury pump and the densimeter are connected together by a valve system.

DESCRIPTION OF THE PREFERRED EMBODIMENTS

Figure 1:
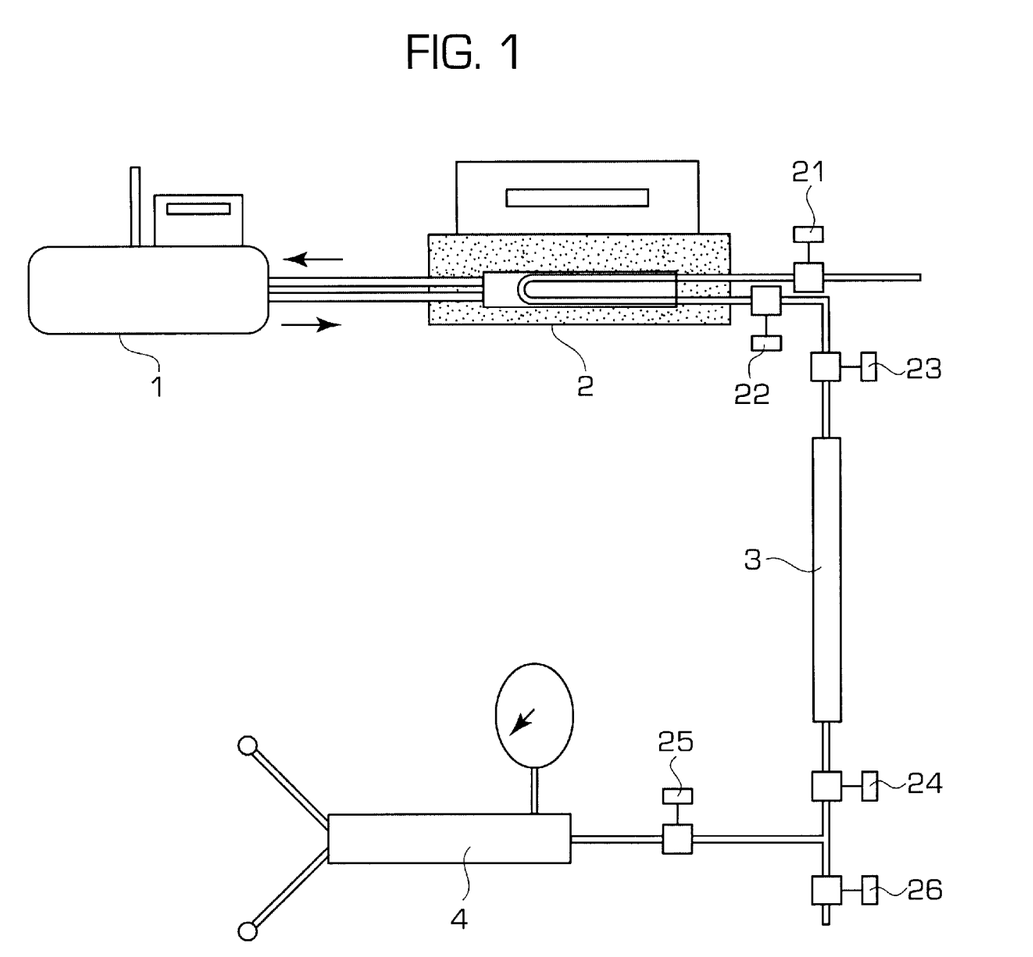
FIG. 1 is a schematic view of an apparatus of this present invention to determine the wax appearance point of dead oils.

A preferred mode of carrying out the present invention is illustrated in FIG. 1, where the wax appearance point is measured for a single petroleum oil composition, either dead or live fluid. The apparatus used to carry out the invention comprises an ultrathermostatic bath 1, a densimeter 2, a supply bottle 3, a mercury pump 4 and valve system made up of valves 21 to 26 to link the circuit comprising the mercury pump 4, the supply bottle 3 and the densimeter 2. The valve system comprises: densimeter outlet valve 21, densimeter inlet valve 22, top bottle valve 23, lower bottle valve 24, mercury pump connection valve 25 and supply valve 26. According to this operating mode of the invention the supply bottle 3 is a cylinder 0.8 cm in diameter and 25 cm high, which yields a 20 cm$^3$ volume. In this case bottle 3 is evacuated and then filled through the valve 26.

In the other preferred mode of the present invention, that is, when the wax appearance point of a live fluid is to be determined, the bottle 3 is replaced by a bottle which already contains the fluid sample collected in the well oil under reservoir conditions (that is, high pressure and dissolved gas). This bottle is a cylinder 10 cm in diameter and 40 cm high, which yields a 600 cm³ volume.

Initially, the ultrathermostatic bath is at a temperature which exceeds the wax appearance point by at least 20° C. The ultrathermostatic bath keeps the desired temperature of the densimeter cell within 0.1° C. Mercury pump 4 transfers fluid from supply bottle 3 to the densimeter cell 2, if necessary with heating. Readings of the oscillation period of the densimeter are effected every ten minutes, at intervals of 1° C., the ten minute period being required for the stabilization of the system. The reading of the oscillation period is converted into a density value by means of the calibration equation of the densimeter. The densimeter is a commercial apparatus model ANTON PAAR DMA512 with which the density of a fluid (oil or gas) can be determined with a precision of $1.10^{-4}$ g/cm³ from the oscillation period of a U-shaped tube (the diapason principle). The natural frequency (f) of the system depends on the specific weight of the fluid contained within the tube ($\rho f$) where:

$$f = \frac{1}{T} = \frac{1}{2\pi}\sqrt{\frac{C}{m_t + \rho f v_t}}$$

wherein T is the temperature, C is the gauging constant of the apparatus and $m_t$ and $v_t$ are respectively the mass and the volume of the tube.

In this embodiment of the invention the influence of pressure on the wax appearance point of fluids having no dissolved gas can be ascertained. By closing the outlet valve 21 of the densimeter 2, the system can be pressurized to the desired pressure by means of the mercury pump 4 and measurements of the oscillation period at the desired temperatures can be obtained.

As described hereinabove, the preferred embodiment of the present invention has accuracy and practicability as main advantages over the prior art processes such as Differential Scanning Calorimetry and rheology or viscosity measuring. This stems from the fact that, being a static measurement, the behavior of the density is more stable than that of viscosity, this latter depending on dynamic parameters. Besides, the densimeter makes it possible to measure density to the fourth decimal place, this accuracy being not reached by the apparatus of the prior art. The optical microscopy method, in spite of being fairly accurate, is not very practical for everyday purposes.

Figure 5:
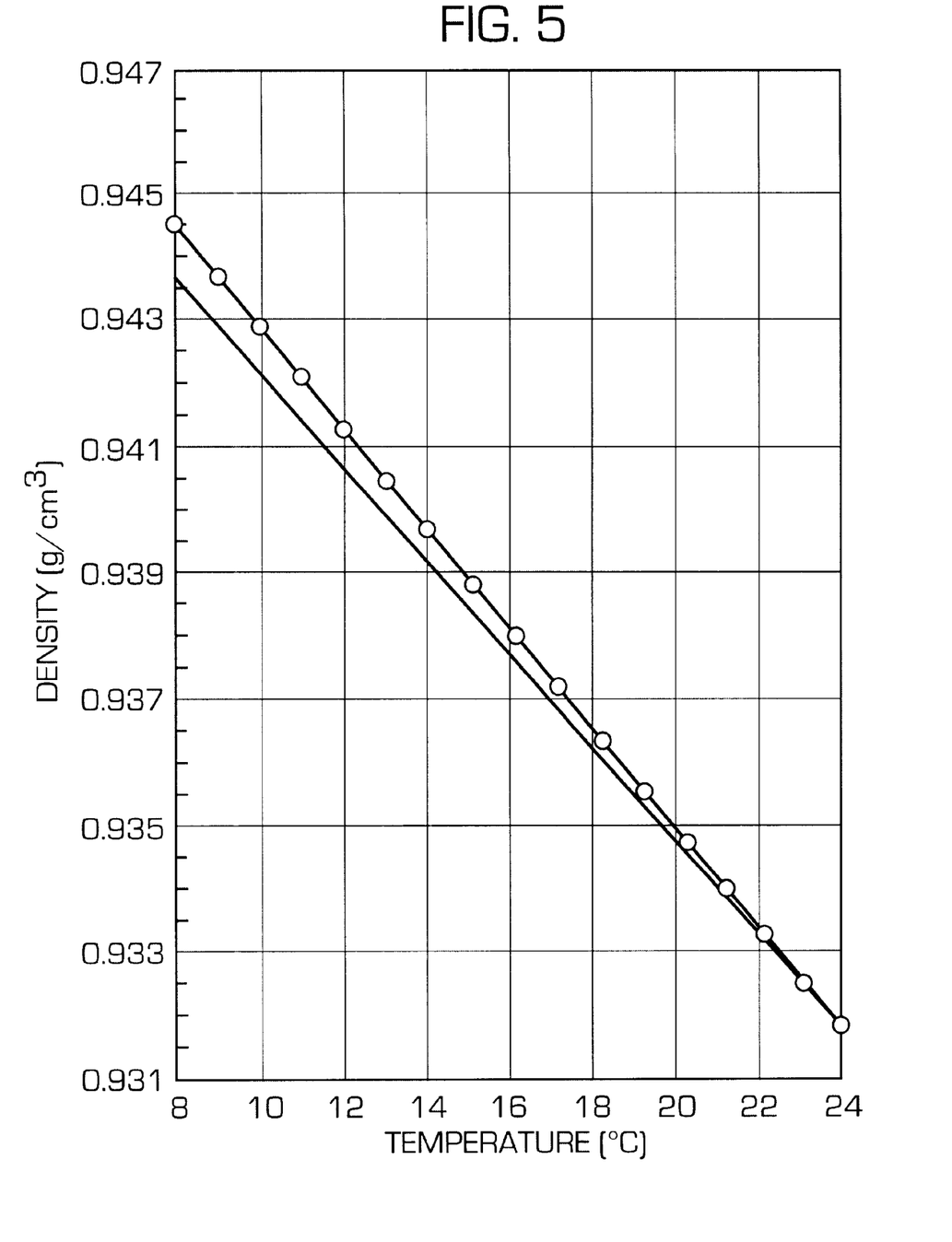
FIG. 5 illustrates the inventive process for an oil containing as low as 0.5 wt % of waxes.

FIG. 5 illustrates a preferred embodiment for the present invention as applied to a dead oil which contains as low as 0.5 wt % paraffins. While the prior art processes for such low-paraffin content oils are inconclusive, the high-precision method of the present invention easily yielded the desired value.

It should be understood that most of the methods for determining the wax appearance point of paraffinic petroleum oils cited in the literature are directed to dead oils, with no dissolved gas. However, using the wax appearance point of dead oils as a parameter in the designing of thermal recovery methods in paraffinic oil reservoirs, or in the designing of production installations (string, lines and separators) can be a drawback to the technical and economical feasibility studies of exploration projects. This is due to the fact that, determining the wax appearance point without taking into consideration the effect of light fractions dissolved in the petroleum oil, fails to represent the actual condition of the petroleum oil in question, since the light fractions dissolved therein increase the solubility of the waxes or paraffins in the liquid phase, therefore reducing the temperature at which the solid phase is formed (that is, the crystallization temperature). Therefore, there is the need for a method which would be easy to perform and which would be directed to determining the live wax appearance point of an as-produced oil, this method and apparatus being provided for by the present invention.

Figure 2:
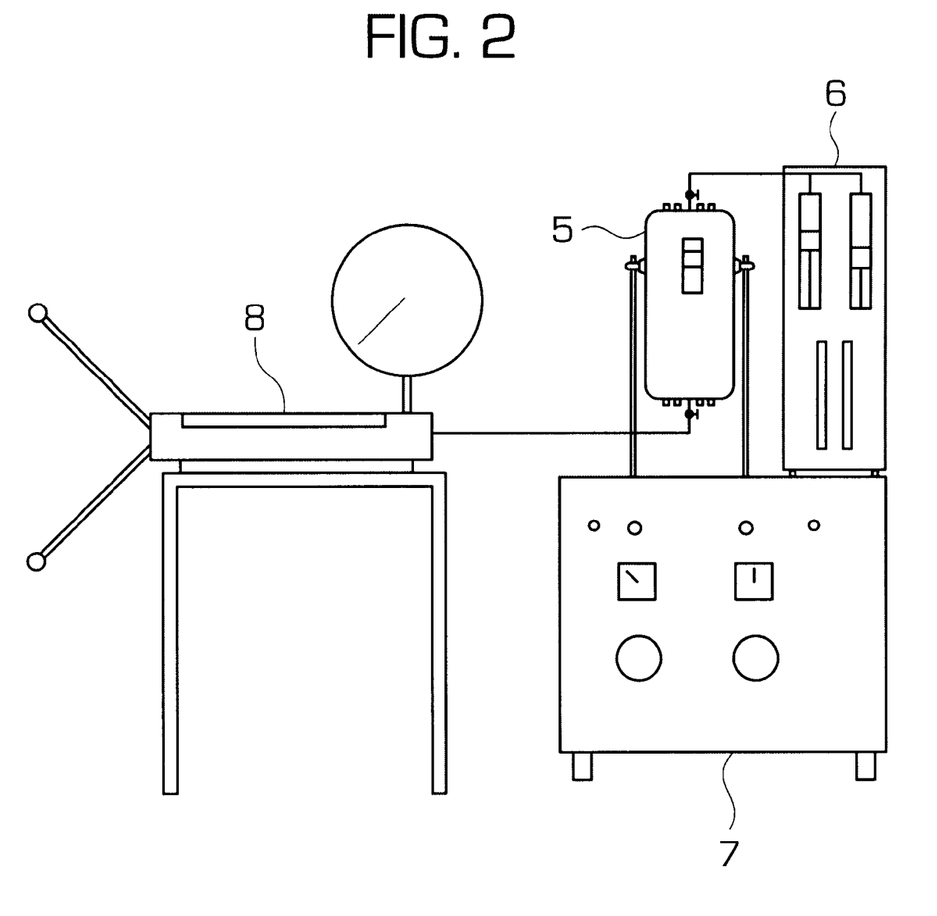
FIG. 2 is a schematic view of a Pressure-Volume-Temperature cell.

Another preferred mode of the present invention is directed to determining the wax appearance point of as-produced oils, that is, petroleum oils containing dissolved gas. As illustrated in FIG. 2, this preferred mode uses a Pressure-Volume-Temperature cell, which comprises a metal cylinder 5 provided with controlled heating (not shown in the Figure), a mechanical agitation system, and glass window to observe the oil within the cell, a collecting means and measuring device 6 to determine the gas volume, a control panel 7 for controlling agitation and temperature, and a mercury pump 8 provided with a manometer. In FIG. 2, the Pressure-Volume-Temperature cell comprises a metallic vessel able to withstand high pressure and temperature, mercury being used as a piston to vary pressure and volume of the petroleum oil contained in the interior of the vessel. In the above form of the invention, during the measurement of the wax appearance point, the gasmeter is substituted for the densimeter. The gasmeter is used only during the release of gas when the oil composition is to be changed. After the release of gas, the Pressure-Volume-Temperature cell is again connected to the densimeter, as explained in detail hereinbelow concerning FIG. 3.

The preferred gas-containing petroleum oil for use with the Pressure-Volume-Temperature cell is an oil having the composition of a reservoir oil, the oil being collected either by bottom sampling by means of a special sampler within the well and near the reservoir face or on the surface by separately collecting the liquid and the separator gas on the surface and recombining them in the laboratory following the conditions of pressure, temperature and separation flowrates.

For the preferred embodiment of the invention which contemplates the presence of dissolved gas, the parameter Solubility ratio (Sr) should be taken into consideration, Sr being the volume of gas dissolved per residual oil volume, at the considered pressure and temperature, both under standard conditions.

Figure 3:
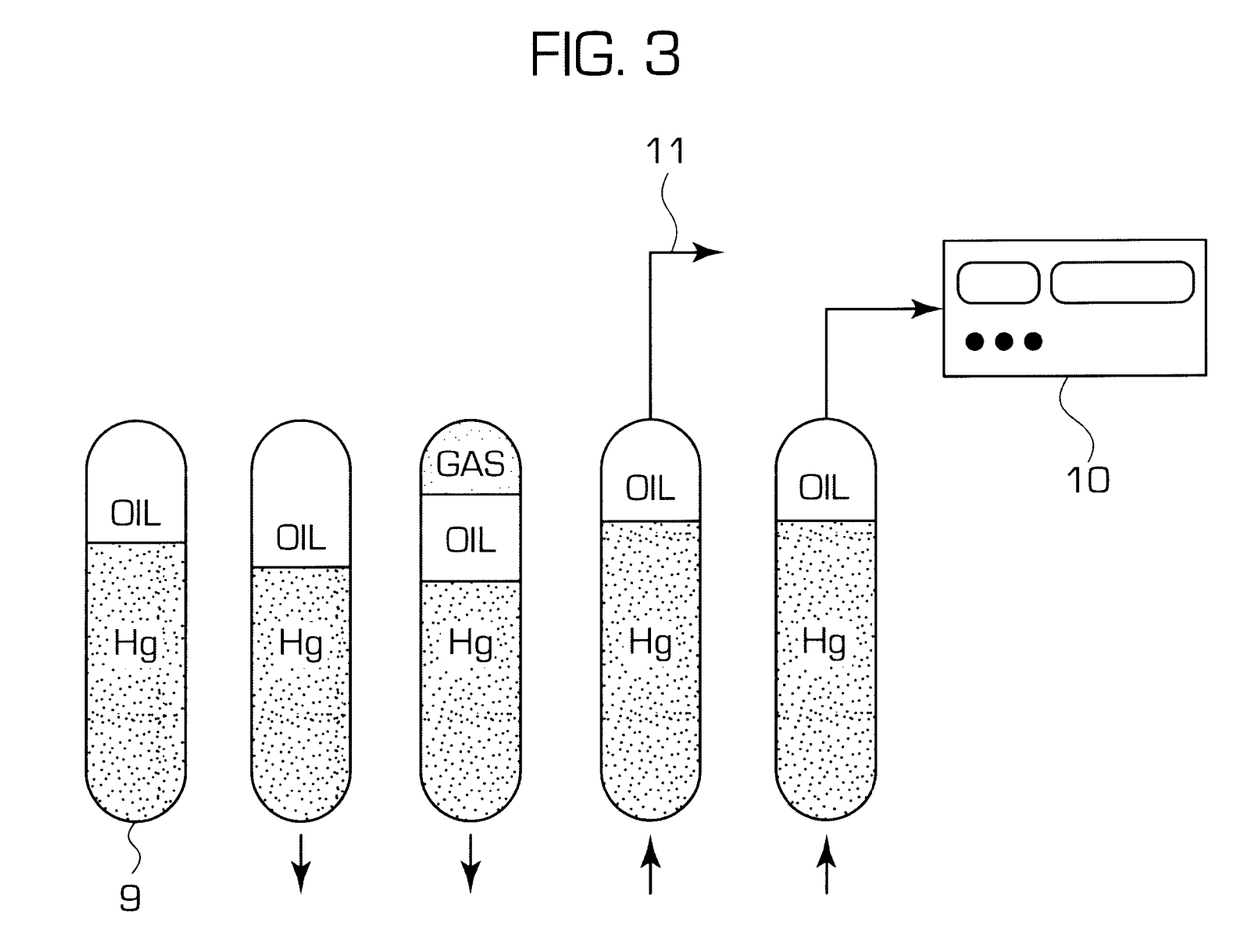
FIG. 3 shows schematically the combined Pressure-Volume-Temperature cell and densimeter for determining the wax appearance point as a function of the solubility ratio (Sr) of the oil.
Figure 4:
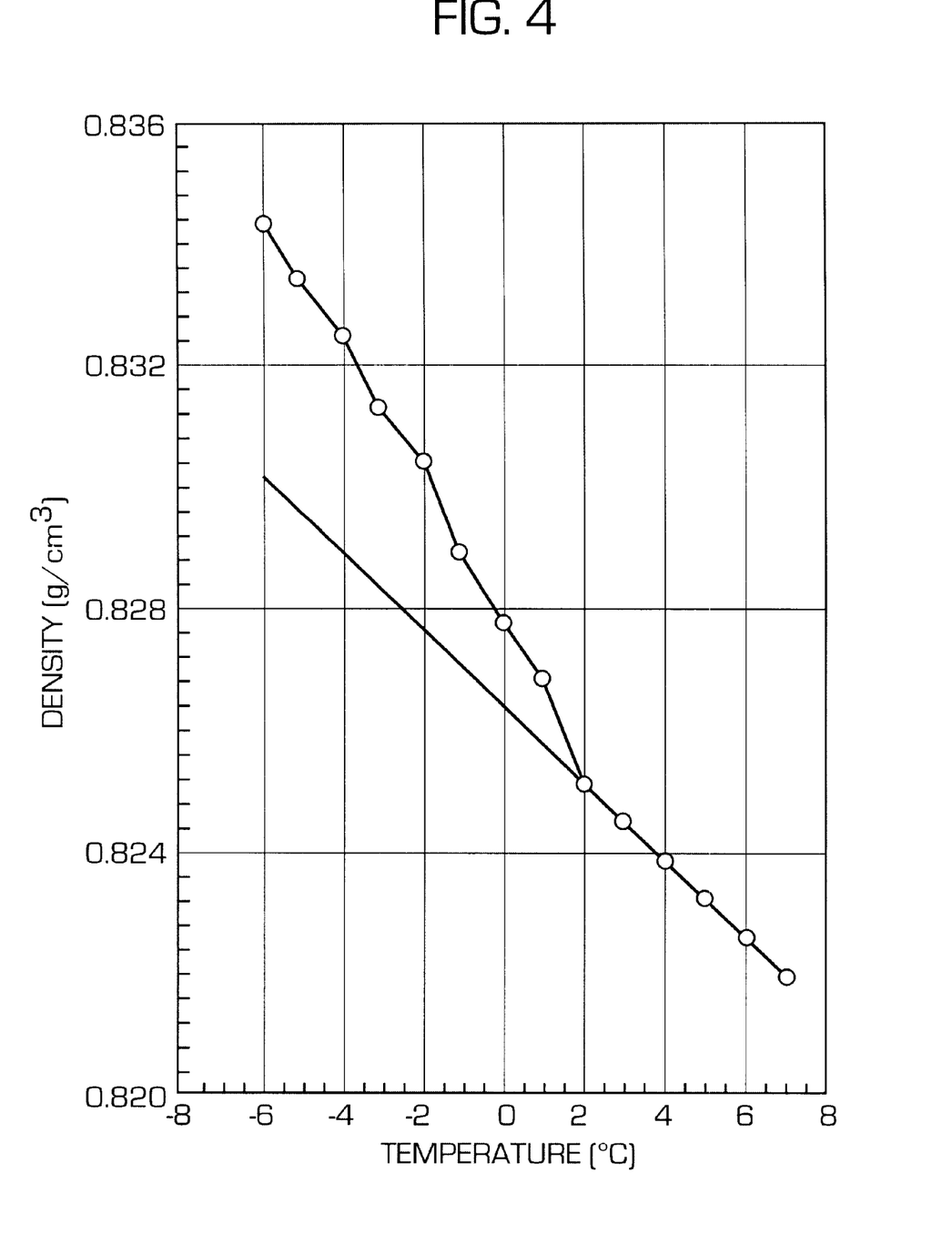
FIG. 4 is a graph to determine the wax appearance point of a diesel oil fluid.

As illustrated in FIG. 3, the method of the present invention which leads to the wax appearance point as a function of the solubility ratio Sr of a petroleum oil comprises, for each Sr, the following steps:

transferring to the Pressure-Volume-Temperature cell 9 a typical reservoir petroleum oil sample at a pressure higher than the saturation pressure (bubble pressure) and without altering the temperature of the sample, the volume of the sample being at least 30 cm³ for each desired depletion stage;

heating the Pressure-Volume-Temperature cell 9 to the reservoir temperature;

after reducing the pressure in the densimeter 10 and the steel lines which link the Pressure-Volume-Temperature cell 9 to the densimeter 10, transferring a sample of the petroleum oil contained in the Pressure-Volume-Temperature cell 9 to the densimeter 10 throughout the heated steel lines in order to obtain the wax appearance point of the oil which contains the whole of the dissolved gas;

for each Solubility ratio, measuring the density, the densimeter readings being obtained every 10 minutes at intervals of 1° C. The reading of the period leads to the density by means of the densimeter gauging equation, as described hereinbefore;

after reading one Solubility ratio, disconnecting the densimeter 10 and the Pressure-Volume-Temperature cell 9, reducing the pressure in the cell by means of a mercury pump to below the bubble pressure, and agitating the cell so as to attain equilibrium between the created gas phase and the liquid phase, the gas released by the cell being transferred to a gasmeter 11 for measuring the volume under atmospheric condition;

reconnecting the densimeter 10 to the Pressure-volume-Temperature cell 9 in order to obtain a new density corresponding to a new Solubility ratio, feeding the densimeter cell with an oil which has been depleted of a certain volume of gas, and measuring the wax appearance point of this gas-depleted petroleum oil;

repeating the procedure for measurement of the density, disconnecting the Pressure-Volume-Temperature cell 9, effecting gas depletion, reconnecting the Pressure-Volume-Temperature cell 9 to the densimeter 10 and again measuring the density so that after successive stages of depletion the petroleum oil is completely deprived of the originally contained gas, so that the oil is at atmospheric pressure, which is the condition for the measurement of the wax appearance point of the dead oil.

Readings of the position of the mercury pump lead to the values for the volume of oil present within the Pressure-Volume-Temperature cell 9 at each depletion stage as well as to the volumes transferred to the densimeter 10. From the volumes of liquid and the volumes of gas released at each depletion stage it is possible to determine the Solubility ratio Sr (volume of gas dissolved in the oil) for the oils formed at each depletion stage.

The present invention will be now illustrated by the following Example, which should not be construed as limiting it.

EXAMPLE

The Barracuda oil field is a giant oil field under exploration by the Brazilian State Oil Company PETROBRAS, the oil field being located at the Campos Basin, in the State of Rio de Janeiro, at a water depth between 600 and up to 1200 meters. The subsea lines used to carry the oil production from the wellhead placed in the sea bottom and up to the platform encounter temperatures as low as 4° C. The oil which leaves the reservoir at 2960 meters depth has a temperature of 86.1° C. and is cooled throughout the process of being produced along the well and the subsea lines. The temperature gradient of the hydrocarbon fluid depends chiefly on its production flowrate and on the temperature outside the line. In the case of long lines, the fluid temperature can be lowered to the temperature of the sea bottom. In order to indicate any plugging which might occur in the lines caused by paraffinic deposits as well as the position of the line where the deposit could occur, the temperature of the petroleum oil at each position should be compared to the wax appearance point of the same oil under the corresponding condition of pressure and flow temperature. Besides the decrease in temperature, a pressure decrease is also noticed along the line with the consequent gradual release of the gas dissolved in the reservoir fluid, the final condition being that of dead oil (without dissolved gas) which is stored under atmospheric pressure. Note that the use of the wax appearance point of the dead oil (which is the more critical condition for paraffins) for indicating the occurrence of precipitation throughout the whole extent of the line can lead to non-representative results. Therefore, under these circumstances it is imperative to determine the wax appearance point under the flow conditions. In order to associate the flow condition of the hydrocarbon fluid to the wax appearance point, an experiment was conducted combining a Pressure-Volume-Temperature cell (which is a metallic vessel able to withstand high pressure and temperature and which uses mercury as a piston in order to vary pressure and volume of the sample under study) to a digital densimeter, also adapted to withstand high pressure and temperature so as to measure the wax appearance point using the method of the present invention.

In this Example a petroleum oil in the reservoir condition was sampled from the well depth, at the face of the producing interval. In this kind of sampling the petroleum oil which is collected contains the whole of the solubilized gas. The sampling was made at the 3-BR-2-RJS well on Jun. 7, 1993. The following procedure was used to obtain the experimental data:

a) the as-collected hydrocarbon fluid from the reservoir was transferred to the Pressure-Volume-Temperature cell at 350 kgf/cm$^2$ at a temperature of 86.1° C.;

b) by withdrawing mercury from the Pressure-Volume-Temperature cell, the pressure of the fluid was carefully reduced until the appearance of the first gas bubble (bubble pressure or saturation pressure).

The experimental value found for the bubble pressure was 138.5 kg/cm$^2$ at 86.1° C.;

c) under this saturation condition, with all the gas dissolved, a first portion of the petroleum oil is transferred to the densimeter, where a wax appearance point of 11° C. is determined;

d) pressure is then reduced to 120.0 kgf/cm$^2$ which is lower than the bubble pressure, this leading to a gas phase. Once the gas-liquid equilibrium has been attained, the gas phase is integrally transferred to a gasmeter, where the volume of gas can be accurately metered under atmospheric conditions. This volume is then corrected to standard conditions (15.56° C. and 760 mm Hg) so as to define a volume V1;

e) under a pressure of 120.0 kgf/cm$^2$, a portion of the depleted oil is transferred to the densimeter which has been connected to the top of the Pressure-Volume-Temperature cell. The new value for the wax appearance point is 13° C.;

f) Steps d) and e) are repeated at the pressures (gauge) of 100.00 kgf/cm$^2$, 80.0 kgf/cm$^2$, 40.0 kgf/cm$^2$, 20.0 kgf/cm$^2$ and finally at atmospheric pressure (dead oil). At steps d) gas volumes named V2, V3, V4, V5 and V6 are measured, corresponding to depletion pressures (gauge) of 100, 80, 40, 20 and 0.0 kgf/cm$^2$ respectively. The residual oil volume in the Pressure-Volume-Temperature cell as measured in the standard conditions 15.6° C. and 760 mm Hg is the reference volume for calculating the solubility ratio Sr. By definition, the solubility ratio at atmospheric pressure is zero. The solubility ratio at 20.0 kgf/cm$^2$ pressure (gauge) is calculated by dividing the volume (V6) of gas which left solution during the reduction in pressure from 20.0 kgf/cm$^2$ to zero by the volume (Vr) of residual oil, that is, Sr (20.0)=V6/Vr. If, at the pressure (gauge) of 20.0 kgf/cm$^2$, oil from the cell has not been supplied to the densimeter, the Solubility ratio at 40.0 kgf/cm$^2$ would be calculated by dividing the total volumes of gas which had left solution during reductions in pressure from 20.0 kgf/cm$^2$ to zero and from 40.0 kgf/cm$^2$ to 20.0 kgf/cm$^2$ by the volume of residual oil: Sr (40.0)= (V5+V6)/Vr. This procedure should be successively repeated up to the bubble pressure, for which the Solubility ratio would be calculated dividing the total volume of released gas (V1+V2+V3+V4+V5+V6) by the volume of residual oil, which is the definition of the overall Solubility ratio of the oil. However, in view of additional intermediate oil withdrawals, the complexity attained by the calculations requires that computer software be adequately written. Note that every volume of oil transferred to the densimeter has a volume of dissolved gas which is not measured in the gasmeter.

Figure 6:
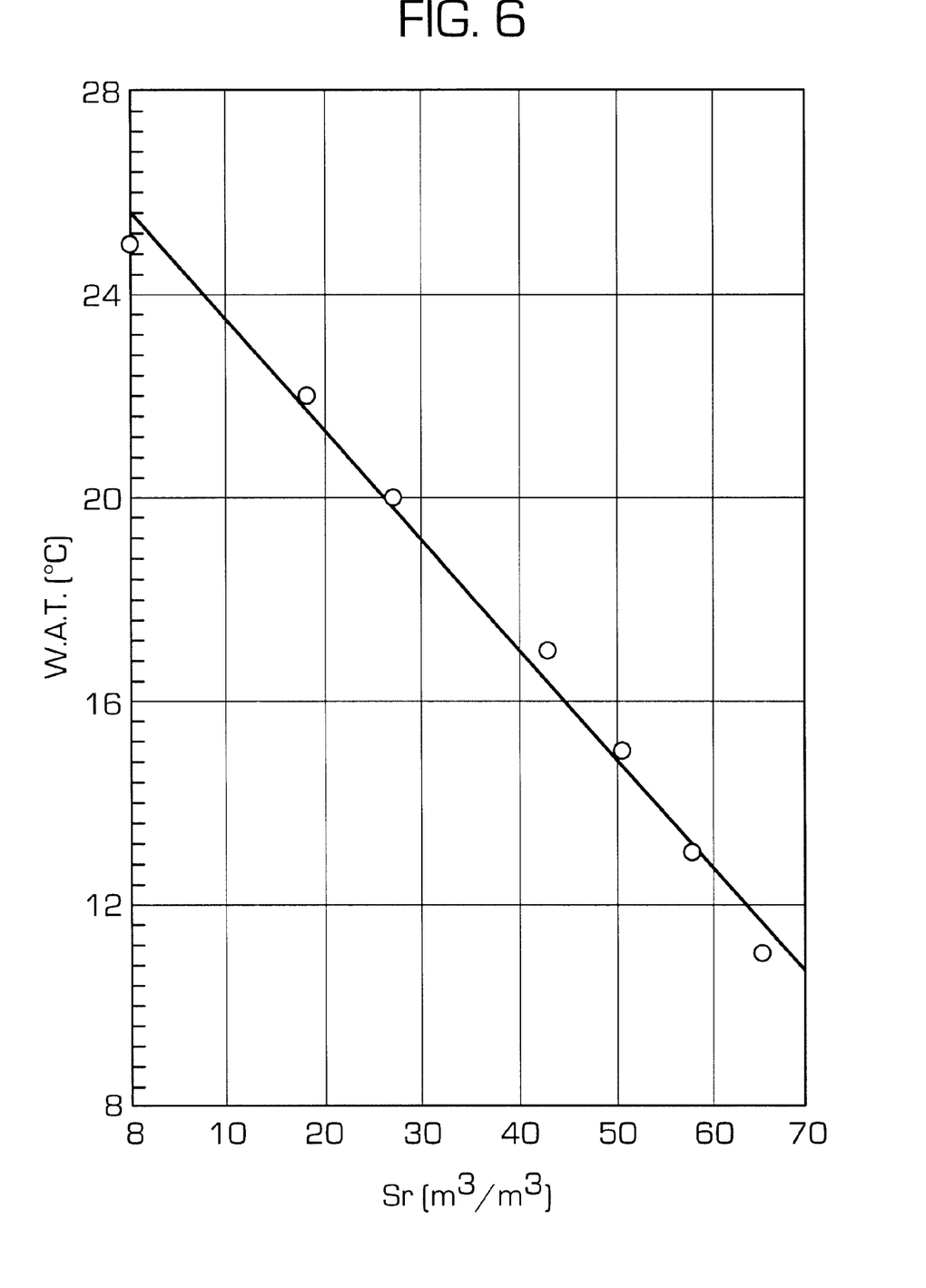
FIG. 6 is a graph illustrating the influence of solubilized gas on the wax appearance point.

TABLE 1 and FIG. 6 show the results obtained for a petroleum oil from the 3-BR-2-RJS well, which contains 3.3 wt % of paraffins, according to the Shell Method Series 1769-88. In column 1 are tabulated the figures for the pressure where the gas was released from the Pressure-Volume-Temperature cell to the gasmeter, and the resulting fluid (petroleum oil) in the cell transferred to the densimeter in order to measure the wax appearance point. Column 2 presents the figures for Solubility ratio Sr which is the volume of gas kept in solution at each pressure stage. The third column lists the figures of wax appearance point determined in the densimeter.

TABLE 1

| Pressure kgf/cm$^2$ | Sr m$^3$/m$^3$ | Wax appearance point ° C. |
|---|---|---|
| 138.5 | 65.07 | 11 |
| 120.0 | 57.84 | 13 |
| 100.0 | 50.54 | 15 |
| 80.0 | 42.96 | 17 |
| 40.0 | 27.35 | 20 |
| 20.0 | 18.58 | 22 |
| 0.0 | 0.0 | 25 |

In order to represent the linear behavior of the experimental points, a straight line equation was determined using linear regression statistical software:

Wax appearance point=25.5−0.215 $Sr$ wherein the correlation coefficient is $R^2$=0.99, that is, a nearly perfect straight line.

Using the inventive method, wax appearance point measurements were effected for dissolved gas-containing reservoir oils of various wax contents. The linear behavior for wax appearance point vs. solubility ratio Sr was repeated for various other oils.

In view of the fact that the difference in wax appearance point between dead oil and dissolved gas-containing oils can be significant, the process of the present invention constitutes an important contribution to the technique of wax appearance point measurement, mainly in the area of dissolved gas-containing oils.

Note that among the prior art methods for the measurement of the wax appearance point of dead oil, only the method based on the viscosity change as a function of temperature could be used for the measurement of the wax appearance temperature of dissolved gas-containing hydrocarbon fluids. However, viscometers such as those of the Rolling Ball type which are normally used in petroleum oil analyses and which infer the viscosity of solubilized gas-containing hydrocarbon fluids through the measurement of the time of fall of an iron sphere, are low-precision instruments which cannot identify the change in the viscosity behavior of low wax content petroleum oils. Besides, in these viscometers, although petroleum oils can be heated, they cannot be cooled to sub-ambient temperatures. Still, as relates to the relationship between the present application and the prior art methods, British GB-A-2268276 as well as the present application are both based on the measurement of the reduction in volume undergone by a hydrocarbon fluid sample as a consequence of a temperature reduction. At the temperature of the onset of wax precipitation, the contraction in volume undergone by the hydrocarbon fluid is stronger, a deviation being observed from the contraction behavior prior to precipitation. Then, this phenomenon is used to determine the wax appearance point, the precision of the measurement being directly related to the experimental accuracy of measuring variations in volume of the sample which could first indicate the occurrence of wax precipitation. However, the method to determine the wax appearance point according to GB-A-2268276 and the method disclosed in the present application are profoundly different. In the technique disclosed in the British publication, the hydrocarbon fluid, whose wax appearance point is to be determined, is kept within a metallic vessel and the volume contraction of the sample due to the wax precipitation is measured by way of a high pressure volumetric pump. It is hypothesized that the precision of such measurement is below the requirements for determining the wax appearance point of hydrocarbon fluids of low wax content. This can be inferred from data of FIG. 2 of the GB-A-2268276, where it can be seen that for a 60 cm$^3$ sample the smallest volume contraction to be determined is 0.017% of the total volume, since the accuracy of the volumetric pump is 0.01 cm$^3$ (0.01× 100%:60 cm$^3$=0.017%). It occurs that this figure is related to the initial wax precipitation of hydrocarbon fluids of high wax content. Thus the method described in GB-A-2268276 seems limited to be applied to hydrocarbon fluids of a rather high wax content, this limitation being overcome by the method described and claimed by the present invention. The high precision of the present method results from the fact that the volume variation of the sample (fluid contraction) is measured by means of the density variation at constant mass. The density is measured by the natural oscillation frequency of the fluid, the accuracy being to the fourth decimal place for a volume of only 1.0 cm$^3$, so that the wax appearance point of low wax content oils can be determined; for example a wax content below 1 wt %, as is the case for the petroleum oils of the Marlim oil field of the Campos Basin, Rio de Janeiro, Brazil.

FIG. 5 illustrates the inventive method for an oil containing as low as 0.5 wt % wax. The measurement of the wax appearance point of such petroleum oil using the prior art methods would be difficult and would show a rather large deviation from the real figure, since these methods lack the necessary accuracy for evaluating the wax appearance point of paraffinic oils of low wax content.

The method and apparatus of the present application also constitute an improvement regarding the way of determining the influence of the fluid composition on the wax appearance point. In this determination the composition of the fluid under study is varied by gradually withdrawing the dissolved gas. According to the apparatus described in GB-A-2268276 several 60 cm$^3$ samples having different amounts of dissolved gas are transferred one at a time to the metallic vessel wherein the wax appearance point is to be determined. Thus, in order to determine the influence of the fluid composition on the wax appearance point at least 1000 cm$^3$ of sample are needed, the petroleum oil being recombined under pressure with varying amounts of dissolved gas.

In the arrangement set forth in the present application, the wax appearance points of various mixtures having different concentrations of dissolved gas are measured by coupling a Pressure-Volume-Temperature cell to the densimeter. The mixtures are prepared in the cell and transferred to the densimeter to determine the wax appearance point. In the method described and claimed herein, the Pressure-Volume- Temperature cell is supplied with the reservoir hydrocarbon fluid (original mixture) and the subsequent mixtures result from the withdrawal of a portion of gas from such fluid. Thus, differently from the prior art methods, which require volumes of up to 1000 cm$^3$, the process of the present invention requires samples of no more than 200 cm$^3$, the various mixtures being obtained with a high degree of accuracy which reduces the experimental work and further speeds the collection of experimental data.

What is claimed is:

1. A method for determining the wax appearance temperature of paraffinic petroleum oils, comprising measuring and plotting a density of the petroleum oil as a function of temperature at constant pressure, and determining a wax appearance point as the temperature at which there is an inflection in a graph of the density as a function of the temperature, wherein density measurements are effected for different amounts of dissolved gas so as to determine a variation in the wax appearance temperature as a function of a solubility ratio equal to the ratio of a volume of gas dissolved at a test pressure and resevoir temperature to a volume of residual oil, both measured under standard conditions.

2. An apparatus for the measurement of the wax appearance temperature of paraffinic petroleum oils, which comprises a bottle to contain a sample of paraffinic oil, a mercury pump for evacuating the bottle and a high pressure and temperature densimeter connected to the bottle for determining a variation in density of the sample with temperature reduction, wherein the densimeter has its temperature regulated by an ultramostatic bath, wherein the bottle, the mercury pump and the densimeter are connected together by a valve, and wherein the bottle is a Pressure-Volume-Temperature cell which uses mercury as a piston to vary the pressure and the volume of the petroleum oil contained within the cell.

3. A method for determining the wax appearance temperature of a paraffinic petroleum oil at different pressures, wherein said petroleum oil comprises dissolved gas at pressures greater than atmospheric, said method comprising the steps of:

(a) measuring and plotting a density of the petroleum oil as a function of temperature at constant pressure, and determining a wax appearance point as the temperature at which there is an inflection in a graph of the density as a function of the temperature, wherein said density is measured by the natural oscillation frequency of a tube in a densimeter containing the petroleum oil;

(b) changing the pressure of the petroleum oil, thereby changing the concentration of dissolved gas in the petroleum oil; and (c) repeating step (a).

4. A method according to claim 3, wherein a wax appearance point is determined for a petroleum oil having the composition of a reservoir oil, and wherein a wax appearance temperature is determined for the dead petroleum oil pertaining to said reservoir oil.

5. A method according to claim 3, wherein wax appearance temperature is determined with an apparatus comprising a densimeter coupled to a Pressure-Volume-Temperature cell.

6. A method according to claim 3, wherein, after step (c), step (b) is repeated at least once followed each time by step (a).

7. A method according to claim 6, wherein step (c) is repeated until the petroleum oil is at atmospheric pressure.

* * * * *